United States Patent

Reiffenrath et al.

Patent Number: 5,204,017
Date of Patent: Apr. 20, 1993

[54] DIFLUOROBENZONITRILES AND LIQUID-CRYSTALLINE MEDIUM

[75] Inventors: Volker Reiffenrath, Rossdorf; Hans-Adolf Kurmeier; Bernhard Scheuble, both of Seeheim-Jugenheim, all of Fed. Rep. of Germany

[73] Assignee: Merck Patent GmbH, Darmstadt, Fed. Rep. of Germany

[21] Appl. No.: 623,387

[22] PCT Filed: Aug. 24, 1990

[86] PCT No.: PCT/EP90/01412
§ 371 Date: Nov. 19, 1990
§ 102(e) Date: Nov. 19, 1990

[87] PCT Pub. No.: WO91/03468
PCT Pub. Date: Mar. 21, 1991

[30] Foreign Application Priority Data

Sep. 7, 1989 [DE] Fed. Rep. of Germany ....... 3929762
Jan. 30, 1990 [DE] Fed. Rep. of Germany ....... 4002609

[51] Int. Cl.$^5$ ............ C09K 19/34; C09K 19/30; C07D 239/02; C07D 213/84
[52] U.S. Cl. ................ 252/299.61; 252/299.63; 252/299.66; 544/242; 544/335; 546/286; 546/301
[58] Field of Search ........... 252/299.1, 299.61, 299.63, 252/299.66; 544/242, 335; 546/286, 301

[56] References Cited

U.S. PATENT DOCUMENTS 4,512,636  4/1985  Andrews et al. ............... 252/299.61
4,551,264 11/1985  Eidenschink et al. ......... 252/299.62
4,853,152  8/1989  Goto ............................... 252/299.63

FOREIGN PATENT DOCUMENTS 62-103057  5/1987  Japan .

Primary Examiner—Robert L. Stoll
Assistant Examiner—Shean C. Wu
Attorney, Agent, or Firm—Millen, White, Zelano & Branigan

[57] ABSTRACT

Difluorobenzonitriles of the formula I

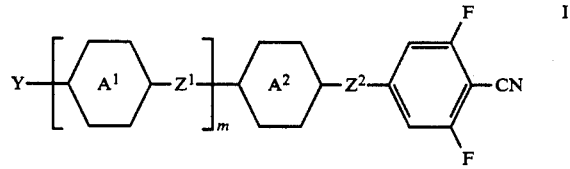

in which
Y is alkyl, alkenyl, alkoxy, oxaalkyl or alkenyloxy containing in each case 1 to 12 carbon atoms,
one of the radicals $A^1$ and $A^2$ present in the molecule is

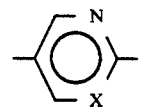

where X is CH or N,
and the other radical $A^1$ or $A^2$ is selected from the group comprising

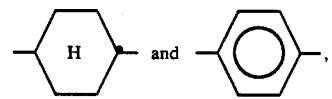

one of the radicals $Z^1$ and $Z^2$ is a single bond and the other radical $Z^1$ or $Z^2$ is —CH$_2$CH$_2$— or a single bond, and
m is 0 or 1, with the proviso that if m=1, $Z^1=Z^2=$ single bond and one of the radicals $A^1$ and $A^2$=2,5-pyrimidinediyl and the other radical $A^1$ or $A^2$=1,4-phenylene, $A^1$ is 2,5-pyrimidinediyl.

14 Claims, No Drawings

DIFLUOROBENZONITRILES AND LIQUID-CRYSTALLINE MEDIUM

SUMMARY OF THE INVENTION

The invention relates to novel difluorobenzonitriles of the formula I

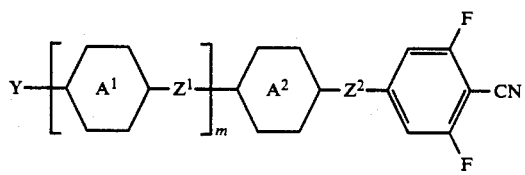

in which
Y is alkyl, alkenyl, alkoxy, oxaalkyl or alkenyloxy containing in each case 1 to 12 carbon atoms,
one of the radicals $A^1$ and $A^2$ present in the molecule is

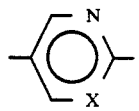

where X is CH or N,
and the other radical $A^1$ or $A^2$ is selected from the group comprising

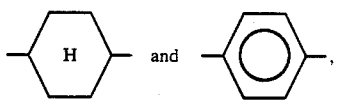

one of the radicals $Z^1$ and $Z^2$ is a single bond and the other radical $Z^1$ or $Z^2$ is —CH$_2$CH$_2$— or a single bond, and
m is 0 or 1, with the proviso that if m=1, $Z^1$=$Z^2$=single bond and one of the radicals $A^1$ and $A^2$=2,5-pyrimidinediyl and the other radical $A^1$ or $A^2$=1,4-phenylene, $A^1$ is 2,5-pyrimidinediyl.

The invention relates furthermore to the use of said compounds as components of liquid-crystalline media and also liquid crystal and electro-optical display components which contain the liquid-crystalline media according to the invention.

The compounds of the formula I can be used as components for liquid-crystalline media, in particular for displays based on the principle of the twisted cell, the guest-host effect, the deformation of aligned phases effect or the dynamic scattering effect.

The object of the invention was to find novel, stable, liquid-crystalline or mesogenic compounds which are suitable as components of liquid-crystalline media and, in particular, at the same time have a comparatively low viscosity and also an extremely high dielectric anisotropy accompanied at the same time by good low-temperature behavior.

It has now been found that compounds of the formula I are eminently suitable as components of liquid-crystalline media. In particular, they have comparatively low viscosities. With their aid, stable liquid-crystalline media with a wide mesophase range and advantageous values for the optical and dielectric anisotropy can be obtained.

Liquid crystals of the formula

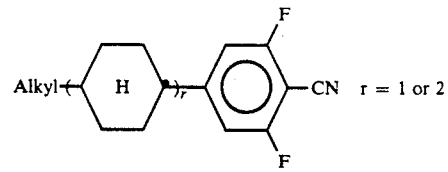

are already known from DE 3,209,178. EP 0,317,175 discloses pyrimidine derivatives of the formula

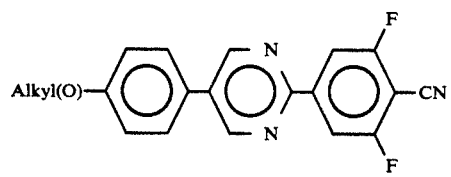

which are, however, notable for very high melting points.

In view of the wide variety of fields of application of those compounds having very high $\Delta\epsilon$, it was, however, desirable to have further compounds available which have properties made-to-measure for the particular applications and have markedly higher values for $\Delta\epsilon$, than the compounds known from DE 3,209,178 and have more beneficial mesophases, better miscibility with other liquid crystals and higher thermal and UV stability than the compounds known from EP 0,317,175.

In addition, the provision of the compounds of the formula I very generally extends appreciably the range of liquid-crystalline substances which are suitable for preparing liquid-crystalline mixtures from various application engineering points of view.

The compounds of the formula I have a wide field of application. Depending on the choice of the substituents, these compounds can serve as base materials from which liquid-crystalline media are predominantly composed; however, compounds of the formula I may also be added to liquid-crystalline base materials from other compound classes in order, for example, to influence the dielectric and/or optical anisotropy of such a dielectric and/or to optimize its threshold voltage and/or its viscosity.

The compounds of the formula I are colorless in the pure state and form liquid-crystalline mesophases in a temperature range which is beneficially situated for electro-optical use. They are stable chemically, thermally and towards light.

The invention consequently relates to the compounds of the formula I and also to the use of said compounds as components of liquid-crystalline media. The invention furthermore relates to liquid-crystalline media having a content of at least one compound of the formula I and also to liquid crystal display components, in particular electro-optical display components which contain such media.

The compounds of the formula I accordingly embrace compounds of the subformulae Ia to Im:

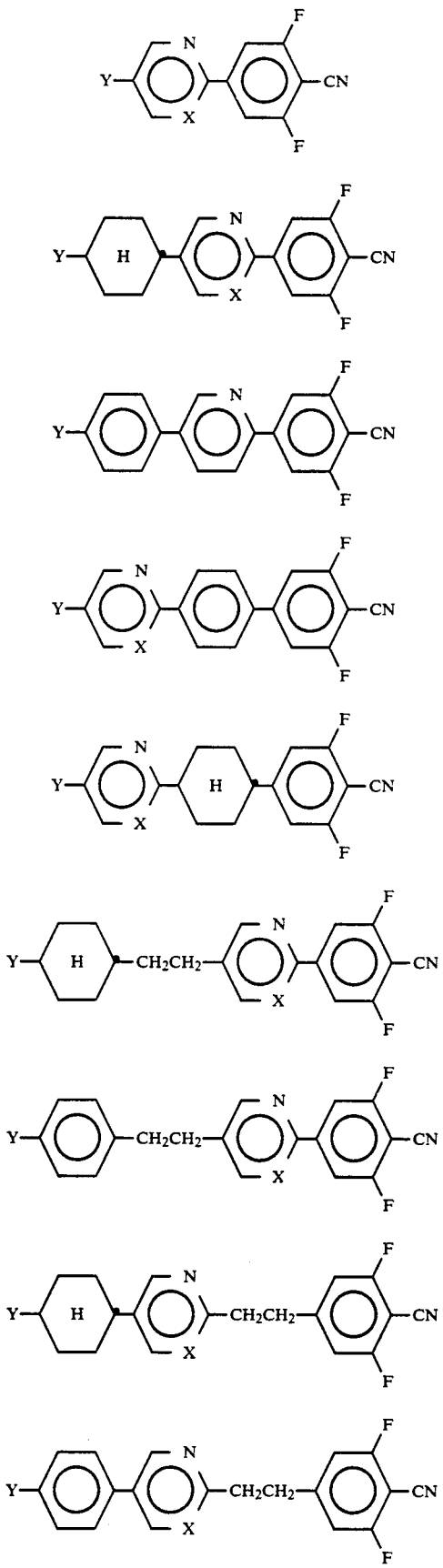

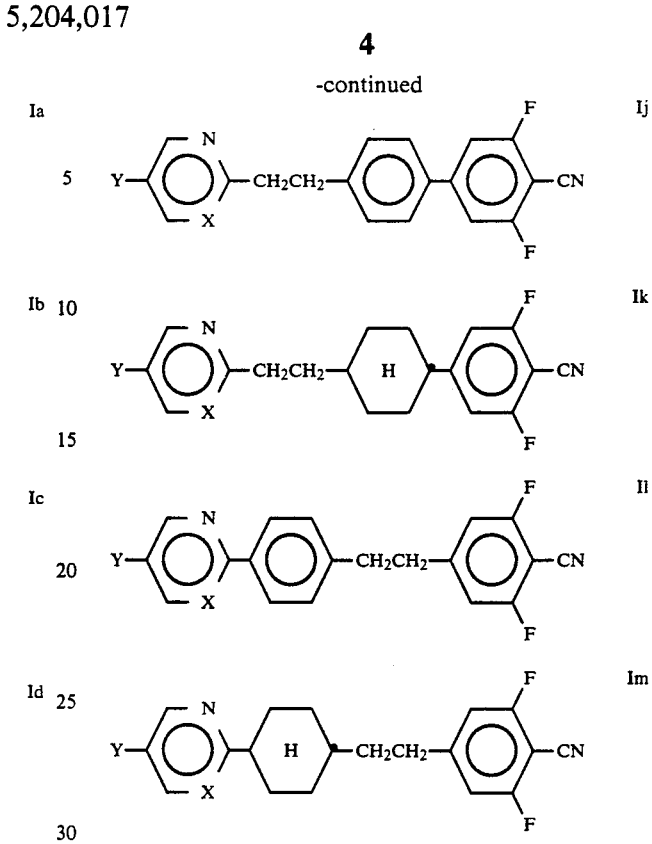

Of these, those of the formulae Ia and Id are particularly preferred.

Y preferably denotes alkyl, and furthermore alkoxy. Preferably, m=1 or, if m=2, $A^1$ is 2,5-pyrimidinediyl and/or one of the radicals $Z^1$ and $Z^2$ is —CH$_2$CH$_2$—.

If Y is an alkyl radical and/or an alkoxy radical, it may be straight-chain or branched. Preferably, it is straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, and furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl preferably is straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If Y is an alkyl radical in which one CH$_2$ group is replaced by —CH=CH—, it may be straight-chain or branched. Preferably, it is straight-chain and has 2 to 10 carbon atoms. It accordingly denotes, in particular, vinyl, 1- or 2-propenyl, 1-, 2- or 3-butenyl, 1-, 2-, 3- or 4-pentenyl, 1-, 2-, 3-, 4- or 5-hexenyl, 1-, 2-, 3-, 4-, 5- or 6-heptenyl, 1-, 2-, 3-, 4-, 5-, 6- or 7-octenyl, 1-, 2-, 3-, 4-, 5-, 6-, 7- or 8-nonenyl, 1-, 2-, 3-, 4-, 5-, 6-, 7-, 8- or 9-decenyl.

Owing to better solubility in the standard liquid-crystalline base materials, compounds of the formulae I having branched wing groups Y may occasionally be of significance, in particular, however, as chiral dopants if they are optically active.

Compounds of the formula I having S$_A$ phases are suitable, for example, for thermally addressed displays.

Branched groups of this type contain as a rule not more than one chain branching. Preferred branched radicals Y are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy.

Formula I embraces both the racemates of these compounds and also the optical antipodes, as well as their mixtures.

Of said compounds of the formula I and also the subformulae, those are preferred in which at least one of the radicals contained therein has one of the specified preferred meanings.

The compounds of the formula I are prepared by methods known per se as are described in the literature (for example, in the standard works such as Houben-Weyl, Methoden der Organischen Chemie, (Methods of Organic Chemistry), Georg-Thieme-Verlag, Stuttgart Volume IX, pages 867 ff.), and in particular, under reaction conditions which are known and suitable for the specified reactions. At the same time, use may also be made of variants known per se and not mentioned in more detail here.

The compounds according to the invention can be prepared, for example, by metalating a compound of the formula II,

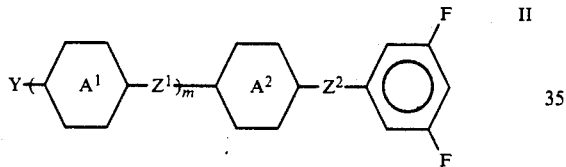

in which Y and Q have the specified meaning, in accordance with the following reaction scheme and then reacting with a suitable electrophile:

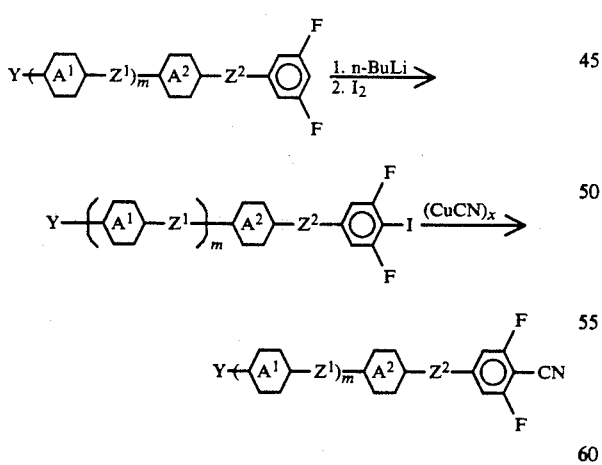

Further synthesis methods are obvious to the person skilled in the art. For example, 1,3-difluorobenzene compounds appropriately substituted in position 5 can be converted in accordance with the above scheme into the 2-cyano-1,3-difluoro compounds and the radical Y-Q- can then be added by reactions which are common in liquid crystal chemistry (for example, esterification, etherification or coupling, for example in accordance with the article of E. Poetsch in Kontakte (Darmstadt) 1988 (2), p. 15).

The compounds of the formula II can, for example, be prepared by the following synthesis scheme:

Scheme 1

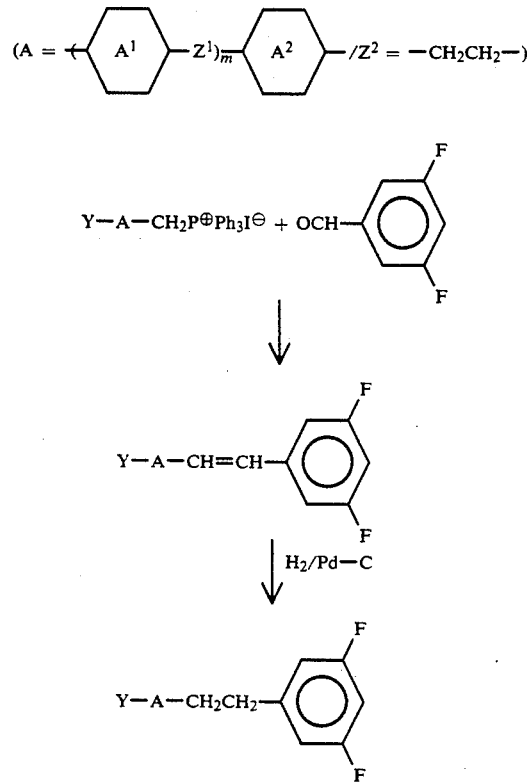

Scheme 2

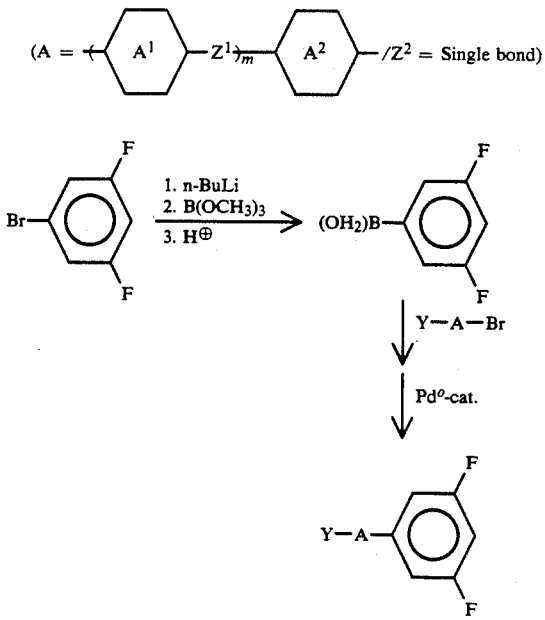

Scheme 3

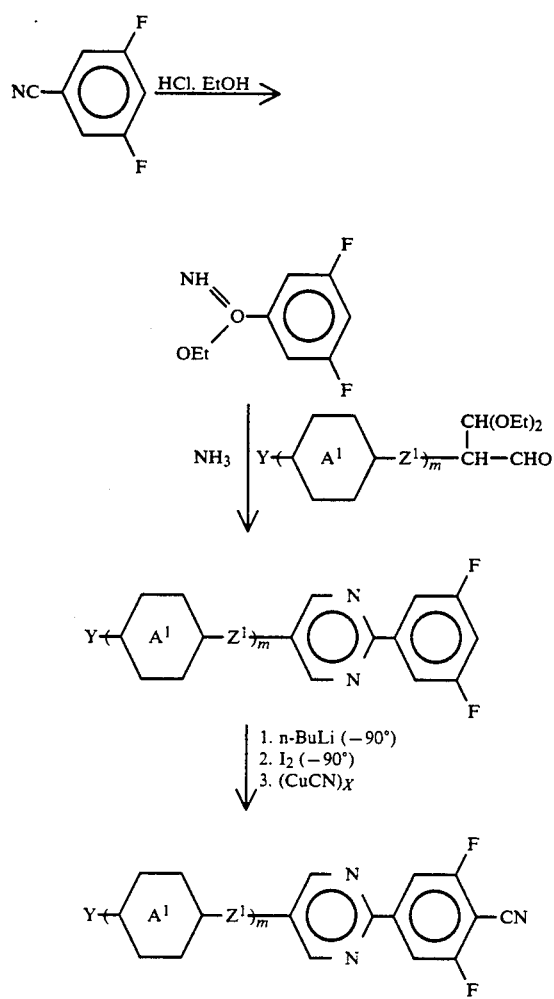

Scheme 4

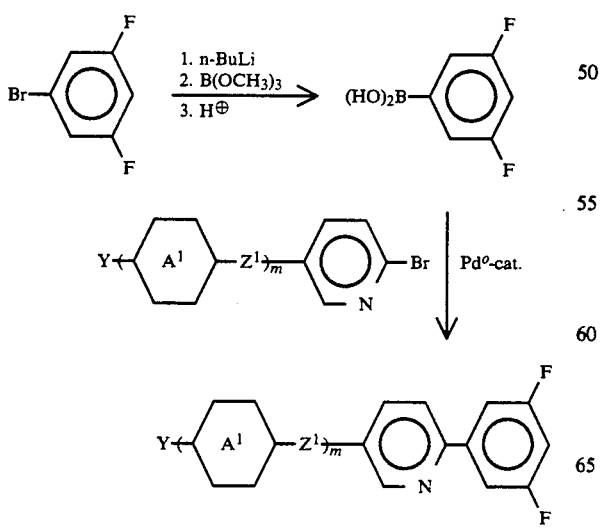

Scheme 5

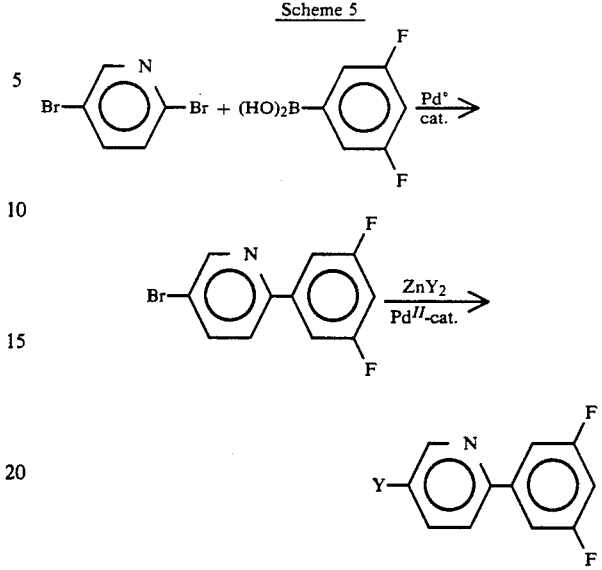

The starting materials are either known or can be prepared by analogy with known compounds.

In addition to one or more compounds according to the invention, the liquid-crystalline media according to the invention preferably contain as further constituents 2 to 40, in particular 4 to 30 components. Very particularly preferably, said media contain 7 to 25 components in addition to one or more compounds according to the invention. These further constituents are preferably selected from nematic or nematogenic (monotropic or isotropic) substances, in particular, substances from the classes of the azoxybenzenes, benzylidene anilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexane carboxylates, cyclohexylphenyl benzoates, cyclohexylphenyl cyclohexylcarboxylates or cyclohexylphenyl cyclohexylcyclohexanecarboxylates, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-biscyclohexylbenzenes, 4,4'-biscycloxhexylbiphenyls, phenyl- or cyclohexylpyrimidines, phenyl- or cyclohexylpyridines, phenyl- or cyclohexyl dioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ether, tolanes and substituted cinnamic acids. The 1,4-phenylene groups in these compounds may also be fluorinated.

The most important compounds suitable as further constituents of the media according to the invention may be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH₂CH₂—E—R" | 4 |

-continued $$R'-L-C\equiv C-E-R'' \qquad 5$$

In the formulae 1, 2, 3, 4 and 5, L and E, which may be identical or different, are, in each case independently of one another, a bivalent radical selected from —Phe—, —Cyc—, —Phe—Phe—, —Phe—Cyc—, —Cyc—Cyc—, —Pyr—, —Dio—, —G—Phe—and —G—Cyc—and also from their group formed as mirror images, where Phe is unsubstituted or fluorine-substituted 1,4-phenylene, Cyc is trans-1,4-cyclohexylene or 1,4-cyclohexenylene, Pyr is 2,5-pyrimidinediyl or 2,5-pyridinediyl, Dio is 1,3-dioxane-2,5-diyl and G is 2-(trans-1,4-cyclohexyl)ethyl, 2,5-pyrimidinediyl, 2,5-pyridinediyl or 1,3-dioxane-2,5-diyl.

Preferably, one of the radicals L and E is Cyc, Phe or Pyr. E is preferably Cyc, Phe or Phe—Cyc. Preferably, the media according to the invention contain one or more components selected from the compounds of the formulae 1, 2, 3, 4 and 5 in which L and E are selected from the group comprising Cyc, Phe and Pyr, and at the same time one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe—and —G—Cyc—, and optionally one or more components selected from the compounds of the formulae 1, 2, 3, 4 and 5 in which the radicals L and E are selected from the group comprising —Phe—Cyc—, —Cyc—Cyc—, —G—Phe—and —G—Cyc—.

In a smaller subgroup of the compounds of the formulae 1, 2, 3, 4 and 5, R, and R" are, in each case independently of one another, alkyl, alkenyl, alkoxy, alkoxyalkyl, alkenyloxy or alkanoyloxy containing up to 8 carbon atoms. Hereinafter this smaller subgroup is called group A and the compounds are designated by the subformulae 1a, 2a, 3a, 4a and 5a. In most of these compounds, R' and R" are different from each other, one of said radicals generally being alkyl, alkenyl, alkoxy or alkoxyalkyl.

In another smaller subgroup, designated as group B, of the compounds of the formulae 1, 2, 3, 4 and 5, R" is —F, —Cl, —NCS or —(O)$_i$CH$_{3-(k+1)}$F$_k$Cl$_1$, where i is 0 or 1 and k+1 is 1, 2 or 3; the compounds in which R" has this meaning are designated by the subformulae 1b, 2b, 3b, 4b and 5b. Particularly preferred are those compounds of the subformulae 1b, 2b, 3b, 4b and 5b in which R" has the meaning —F, —Cl, —NCS, —CF$_3$, —OCHF$_2$ or —OCF$_3$.

In the compounds of the subformulae 1b, 2b, 3b, 4b and 5b, R' has the meaning specified for the compounds of the subformulae 1a-5a and is preferably alkyl, alkenyl, alkoxy or alkoxyalkyl.

In a further smaller subgroup of the compounds of the formulae 1, 2, 3, 4 and 5, R" is —CN; this subgroup is hereinafter designated as group C and the compounds of this subgroup are correspondingly described by subformulae 1c, 2c, 3c, 4c and 5c. In the compounds of the subformulae 1c, 2c, 3c, 4c and 5c, R' has the meaning specified for the compounds of the subformulae 1a-5a and is preferably alkyl, alkoxy or alkenyl.

In addition to the preferred compounds of the groups A, B and C, other compounds of the formulae 1, 2, 3, 4 and 5 having other variants of the substituents envisaged are also common. All these substances are obtainable by methods known from the literature or by analogy thereto.

In addition to compounds according to the invention of the formula I, the media according to the invention preferably contain one or more compounds which are selected from the group A and/or group B and/or group C. The proportions by mass of the compounds from these groups in the media according to the invention are preferably:

| Group A: | 0 to 90%, preferably 20 to 90%, in particular 30 to 90% |
| Group B: | 0 to 80%, preferably 10 to 80%, in particular 10 to 65% |
| Group C: | 0 to 80%, preferably 5 to 80%, in particular 5 to 50% | the sum of the proportions by mass of the compounds contained in the respective media according to the invention and selected from the groups A and/or B and/or C being preferably 5%-90% and in particular 10% to 90%.

The media according to the invention preferably contain 1 to 40% and particularly preferably 5 to 30% of compounds according to the invention. Furthermore, media containing more than 40% and in particular 45 to 90% of compounds according to the invention are preferred. The media preferably contain three, four or five compounds according to the invention.

The media according to the invention are prepared in a manner conventional per se. As a rule, the components are dissolved in one another, expediently at elevated temperature. The liquid-crystalline phases according to the invention can be modified by suitable additives in a manner such that they can be used in all the types of liquid crystal display components hitherto known. Such additives are known to the person skilled in the art and are comprehensively described in the literature (H. Kelker/R. Hatz, Handbook of Liquid Crystals, Verlag Chemie, Weinheim, 1980). For example, pleochroic dye-stuffs can be added to produce colored guest-host systems or substances can be added to modify the dielectric anisotropy, the viscosity and/or the orientation of the nematic phases.

EXAMPLES

The following examples are intended to illustrate the invention without limiting it. Above and below the power (sic) data are percent by weight. All temperatures are specified in degrees Celsius. Mp is melting point, Cp=clearing point. Furthermore, C=crystalline state, N=nematic phase, S=smectic phase and I=isotropic phase. The data between these symbols are the transition temperatures. $\Delta n$ is optical anisotropy (589 nm, 20° C.) and the viscosity (mm$^2$/sec) was determined at 20° C.

"Conventional working-up" means: water is added if necessary, extraction is carried out with methylene chloride, diethyl ether or toluene, separation is carried out, the organic phase is dried, evaporation is carried out and the product is purified by distillation under reduced pressure or crystallization and/or chromatography. The following abbreviations are used:

| n-BuLi | n-butyllithium |
| DAST | diethylaminosulfur trifluoride |
| DCC | dicyclohexylcarbodiimide |

| | |
|---|---|
| DDQ | dichlorodicyanobenzoquinone |
| DIBALH | diisobutylaluminium hydride |
| KOT | potassium tert.-butanolate |
| THF | tetrahydrofuran |
| pTSOH | p-toluenesulfonic acid |
| TMEDA | tetramethylethylenediamine |

EXAMPLE 1

0.1 m of n-BuLi (1,5 M in hexane) is added dropwise to a solution of 0.1 m of 1-[p-(5-n-propyl-2-pyrimidinyl)-phenyl]-2-(3,5-difluorophenyl)ethane (prepared in accordance with scheme 1) and 0.1 m of TMEDA in 300 ml of THF at approximately −90°. Stirring is carried out for a further 30 min at this temperature and then a solution of 0.1 m of $I_2$ in 70 ml of THF is slowly added. After addition is complete, the solution is allowed to heat up to −20° and hydrolyzation is carried out with $H_2O$. The product is completely dissolved by adding diethyl ether and excess $I_2$ is removed by washing with sodium thiosulfate solution and $H_2O$. After evaporating down, the product is left behind as a residue and without further purification, is heated with 0.12 m of $(CuCN)_x$ and 100 ml of NMP for 4 h at 170° C. in an oil bath. After this time, water and $CH_2CH_2$ are added to the cooled reaction mixture, and the organic phase is washed, dried and evaporated down. The pure product can be obtained by chromatography and crystallization. 1-[p-(5-n-propyl-2-pyrimidinyl)-phenyl]-2-(4-cyano-3,5difluorophenyl)ethane is obtained.

EXAMPLES 2 to 24

The following compounds according to the invention are obtained analogously from the corresponding precursors of the formula II:

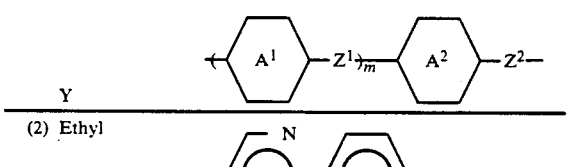

| Y | |
|---|---|
| (2) Ethyl | 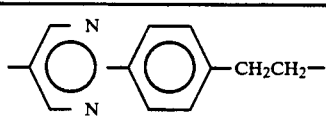 |
| (3) n-Butyl | 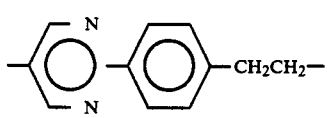 |
| (4) n-Pentyl | 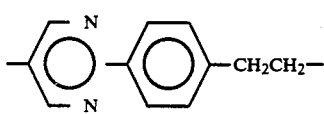 |
| (5) n-Heptyl | 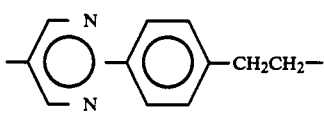 |
| (6) n-Heptyl | 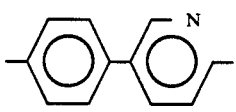 |

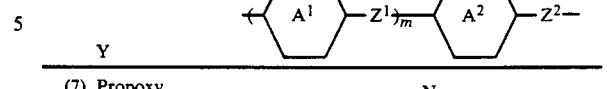

| Y | |
|---|---|
| (7) Propoxy | 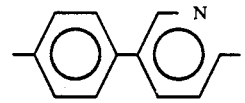 |
| (8) Butoxy |  |
| (9) n-Propyl |  |
| (10) n-Pentyl | 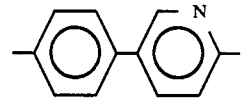 |
| (11) Methoxymethyl |  |
| (12) n-Propyl | 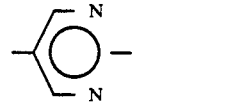 |
| (13) n-Pentyl | 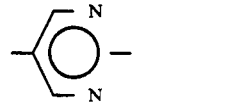 |
| (14) n-Propyl | 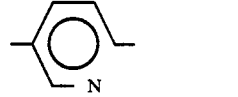 |
| (15) n-Pentyl |  |
| (16) n-Propyl | 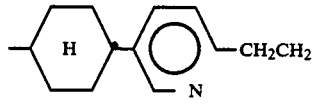 |
| (17) n-Butyl | 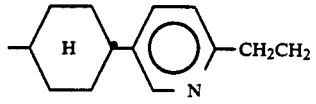 |
| (18) n-Pentyl | 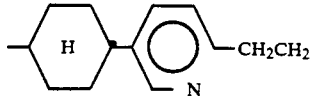 |

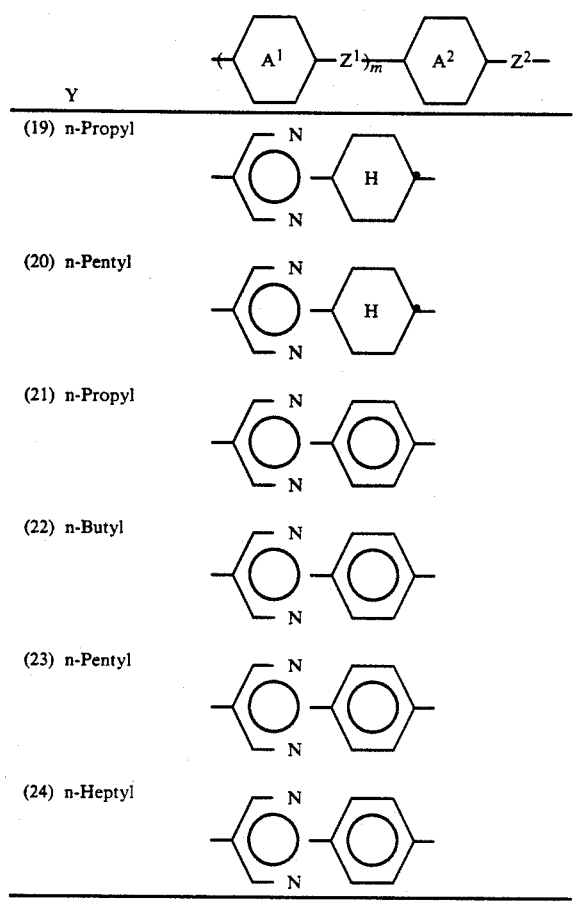

$Z^2$ is a single bond;
$Z^1$ is —CH$_2$CH$_2$— or a single bond; and
m is 0 or 1,
with the proviso that if m is 1, $Z^1$ is a single bond, one of the radicals $A^1$ and $A^2$ is 2,5-pyrimidinediyl and the other of $A^1$ and $A^2$ is 1,4-phenylene, then $A^1$ is 2,5-pyrimidinediyl and $A^2$ is 1,4-phenylene; if m is 0, then $A^2$ is

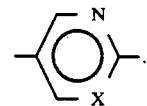

2. In a liquid-crystalline medium containing at least two liquid-crystalline components, the improvement wherein at least one of said components is a compound according to claim 1.

3. In an electro-optical display device containing a liquid-crystalline medium, the improvement wherein said display device contains a medium according to claim 2.

4. In a method of generating an electro-optical display using a display device, the improvement wherein said device is one of claim 3.

5. A compound according to claim 1, wherein said compound is of subformulae Ia, Ib, Ic, If or Ig

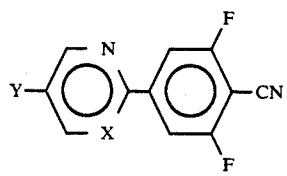 Ia

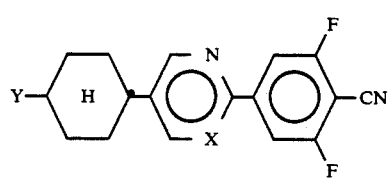 Ib

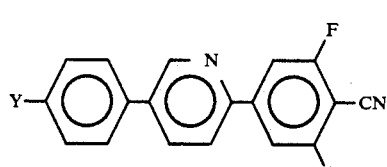 Ic

We claim:
1. A difluorobenzonitrile compound of formula I

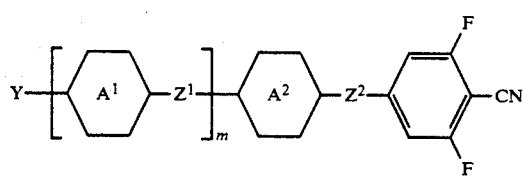 I wherein
Y is alkyl, alkenyl, alkoxy, oxaalkyl or alkenyloxy, in each case containing 1–12 carbon atoms;
one of $A^1$ and $A^2$ which is present in the compound is

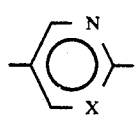

and the other of $A^1$ and $A^2$ is

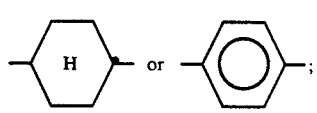

x is CH or N;

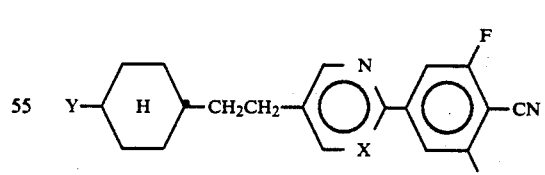 If

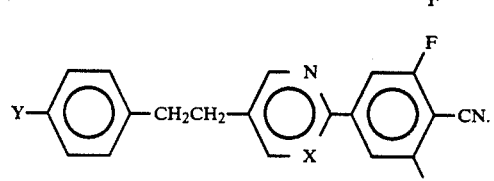 Ig

6. A compound according to claim 1, wherein said compound is of the subformulae Id, Ie, Ij or Ik

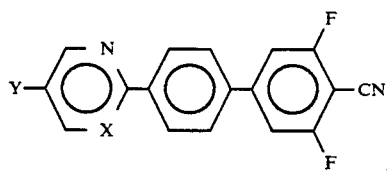 Id

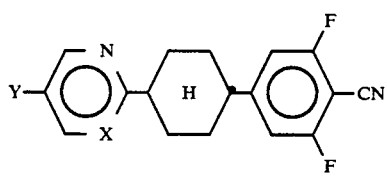 Ie

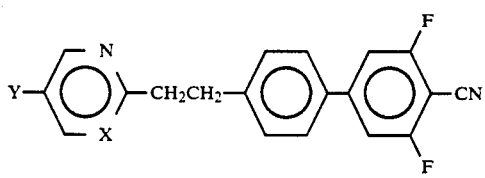 Ij

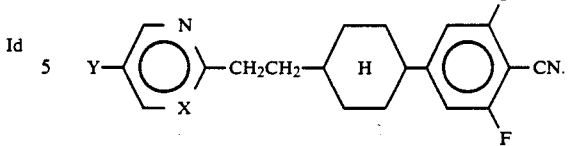 Ik

7. A compound according to claim 1, wherein Y is alkyl.

8. A compound according to claim 1, wherein Y is alkoxy.

9. A compound according to claim 1, wherein Y is oxaalkyl.

10. A compound according to claim 1, wherein Y is an alkyl radical in which one $CH_2$ group is replaced by —CH=CH—.

11. A compound according to claim 1, wherein said compound exhibits a $S_a$ phase.

12. A liquid-crystalline medium according to claim 2, wherein said medium contains 1–40% of compounds according to formula I.

13. A liquid-crystalline medium according to claim 2, wherein said medium contains 45–90% of compounds according to formula I.

14. A liquid-crystalline medium according to claim 2, wherein said medium contains 3–5 compounds of formula I.

* * * * *